(12) United States Patent
Uto et al.

(10) Patent No.: US 7,305,015 B2
(45) Date of Patent: Dec. 4, 2007

(54) ULTRAVIOLET LASER-GENERATING DEVICE AND DEFECT INSPECTION APPARATUS AND METHOD THEREFOR

(75) Inventors: Sachio Uto, Yokohama (JP); Minoru Yoshida, Yokohama (JP); Toshihiko Nakata, Hiratsuka (JP); Shunji Maeda, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 141 days.

(21) Appl. No.: 10/888,980

(22) Filed: Jul. 13, 2004

(65) Prior Publication Data

US 2004/0240493 A1 Dec. 2, 2004

Related U.S. Application Data

(63) Continuation of application No. 09/764,457, filed on Jan. 19, 2001, now Pat. No. 6,765,201.

(30) Foreign Application Priority Data

Feb. 9, 2000 (JP) .............................. 2000-038124

(51) Int. Cl.
*H01S 3/10* (2006.01)
(52) U.S. Cl. .......................................... 372/22; 372/21
(58) Field of Classification Search ...................... None
See application file for complete search history.

(56) References Cited

U.S. PATENT DOCUMENTS

| | | | |
|---|---|---|---|
| 4,644,172 A | 2/1987 | Sandland et al. | |
| 5,832,009 A | 11/1998 | Kikuchi | |
| 5,988,161 A * | 11/1999 | Kroll | 128/202.12 |
| 6,002,697 A * | 12/1999 | Govorkov et al. | 372/34 |
| 6,215,806 B1 * | 4/2001 | Ohmi et al. | 372/57 |
| 6,411,377 B1 * | 6/2002 | Noguchi et al. | 356/237.4 |
| 2002/0061032 A1 * | 5/2002 | Miura et al. | 372/4 |
| 2002/0148961 A1 | 10/2002 | Nakasuji | |

FOREIGN PATENT DOCUMENTS

| | | |
|---|---|---|
| JP | 01-135756 | 9/1989 |
| JP | 3-200939 | 9/1991 |
| JP | 7-261091 | 10/1995 |
| JP | 11-167132 | 6/1999 |

* cited by examiner

*Primary Examiner*—Dung Nguyen
(74) *Attorney, Agent, or Firm*—Antonelli, Terry, Stout & Kraus, LLP.

(57) ABSTRACT

An ultraviolet laser-generating device, for use in a defect inspection apparatus and a method thereof, etc., comprising: a laser ray source for irradiating and emitting a basic wave of laser ray therefrom; a wavelength converter device for receiving the basic wave of laser ray emitted from the laser ray source and for converting it into an ultraviolet laser ray composed of a multiplied high harmonic light of the basic wave of laser ray; and a container having an inlet window, upon which the basic wave of laser ray emitted from the laser ray source is incident upon, and an outlet window for emitting the ultraviolet laser ray composed of the multiplied high harmonic light of the basic wave of laser ray, and installing the wavelength converter device therein, wherein the container is hermetically sealed and is filled up with an inert gas, such as nitrogen or argon gas, therein.

8 Claims, 15 Drawing Sheets

ULTRAVIOLET LASER-GENERATING DEVICE AND DEFECT INSPECTION APPARATUS AND METHOD THEREFOR

CROSS REFERENCE TO RELATED APPLICATION

This is a continuation of U.S. application Ser. No. 09/764,457, filed Jan. 19, 2001, now U.S. Pat. No. 6,765,201, the subject matter of which is incorporated by reference herein.

BACKGROUND OF THE INVENTION

1. Field of the Invention

The present invention relates to an ultraviolet laser-generating device, generating an ultraviolet laser beam or ray to be used for inspection or observation of minute pattern defects, foreign matters, etc., in the fabrications of, such as, semiconductor devices and a flat panel display, representatively, and further relates to a defect inspection apparatus and a method therefor, with using the ultraviolet laser ray obtained therefrom, thereby enabling detection of defects with high resolution, as well as a method for maintenance thereof.

2. Description of Prior Art

For example, circuit patterns formed on the semiconductor devices tends to be fine or minute, more and more, as the technology advance in the high integration thereof. In particular, masks and reticules, used in a process of photolithography for manufacturing of the semiconductor devices, as well as the defects of the patterns on a wafer, on which such as the circuit patterns of those are transcribed through exposure, are required to be detected with such the increasing high resolution. As a method for increasing the resolution, there can be listed up a way of shortening the wavelength of an illumination light from region of visible lights to that of ultraviolet lights. Conventionally, as a light source was used or applied, such as a mercury lamp, a Xenon lamp, etc., and only the light having a required wavelength(s) is/are selected optically from the various bright lines (or emission lines) of the lamp, to be applied thereto.

However, for the bright lines of the lamp, there are problems that it is difficult to compensate chromatic aberrations of an optic system due to wide range or width of the emission spectrum thereof, and that the light source comes to be large in size so as to obtain sufficient intensity of illumination, so that it has a bad or low efficiency, etc. In recent years, an exposure apparatus has been developed, installing a light source, KrF eximer laser of 248 nm in wavelength, as a light source thereof for use in manufacturing of the semiconductors, however there are also problems that the eximer laser ray source comes to be large in size thereof, and that it necessitates a certain countermeasure since it uses a fluorine gas therein, etc. Because of this, as the light source of such the ultraviolet (UV) laser ray other than the above-mentioned, YAG laser beam is converted in the wavelength by means of a non-linear optical crystal, thereby obtaining the third ($3^{rd}$) high harmonic (355 nm) or the fourth ($4^{th}$) high harmonic (266 nm) therefrom.

A wavelength converter device, obtaining the UV laser ray in this manner is already known by, such as, Japanese Patent Laying-Open No. Hei 8-6082 (1996) <prior art 1>, Japanese Patent Laying-Open No. Hei 7-15061 (1995) <prior art 2>, Japanese Patent Laying-Open No. Hei 11-64902 (1999) <prior art 3>, and Japanese Patent Laying-Open No. Hei 11-87814 (1999) <prior art 4>.

In the prior art 1 is described the wavelength converter device, comprising: resonance means, being positioned at an exit side of a light emission means for emitting a light having basic wavelength, having a resonance frequency corresponding to a resonance length, which is obtained by setting the length of an optical path, through which the light propagates, as said the resonance length, and a plural number of reflection means for reflecting said light in an inside thereof; a non-linear optical material, being positioned on the optical path of the light propagating through the inside of said resonance means, having an anisotropic property therewith, and for emitting the light being incident thereupon and at least one light converted in wavelength, being different from said light in the wavelength thereof; and an electric field applying means for applying an electric field to said non-linear optical material, so that the resonance frequency of said resonance means is in synchronism with the light of said basic wavelength, thereby generating the UV laser ray.

Also, in the prior art 2 is described the wavelength converter device, comprising: a light source for supplying a laser ray; an optical resonator for resonating a laser ray generated from said light source; a non-linear optical material, being positioned within said optical resonator, for converting the laser ray into a light wave having wavelength which is shorter than that thereof; and an optical system for feeding back said laser ray emitted from said optical resonator to said light source via the optical resonator, again, wherein said optical resonator, said non-linear optical material and said optical system are disposed within a vacuum container.

Also, in the prior art 3 is described the wavelength converter device of an outer resonation type, wherein, in a space defined between a wavelength converter element (for example, a non-linear optical crystal) and an optical member for separation of the laser ray (for example, a mirror having wavelength selectability therewith) is provided a material, which is optically transparent, or it is filled up with air or inactive gas, etc., or is kept into a substantial vacuum condition, so as to cut off or insulate a portion defined between said wavelength converter element and the optical member for separation of the laser beam, from an outside, thereby preventing dusts and/or gas components from adhering and/or deposing on a light emission surface for the laser ray of said wavelength converter element and/or a light receiving surface of said optical member for separation of the laser ray.

And, the prior art 4 also describes an extension or prolongation in lifetime of the laser resonator, by removing contaminating materials, such as oil, etc., adhered on the mirror, which constructs the laser resonator, and/or on the component of the non-linear optical crystal, substantially.

SUMMARY OF THE INVENTION

However, in the wavelength converter device, a very little amount of active gas, generated when the ultraviolet light is incident upon the optical members, such as, all of the mirrors, etc., which are provided within the optical resonator, or upon the surface of the non-linear optical crystal, and when it is incident upon suspended or floating matters staying behind within the optical resonator, adheres upon the surfaces of the optical members, such as the mirrors, etc., and/or the non-linear optical crystal, later, thereby bringing about a problem of decreasing the permeability thereof, etc.

For dissolving such the problems, according to the prior art 2 mentioned above, the optical resonator, the non-linear optical material and the optical system are disposed within the vacuum container. However, since the optical resonator, the non-linear optical material and the optical system are disposed within the vacuum container, according to the prior art 2, though it is possible to protect the optical resonator, the non-linear optical material and the optical system from the contamination thereof, it is necessary to make the vacuum container secure so that no deformation due to internal stress will occur the inside of the optical resonator, the non-linear optical material and the optical system, as well as to make a seal construction certain. As a result thereof, it has a drawback that the vacuum container comes to be complex in the structure thereof, including the seal construction thereof, etc. Further, according to the prior art 2, as described in the Japanese Patent Laying-Open No. Hei 7-15061 (1995), there is a necessity of controlling the increasing temperature of the non-linear optical crystal, and because of this, heat fills up inside the vacuum container, therefore it has a drawback of giving an ill influence upon the optical member(s), such as other mirror(s), etc.

Also, in the prior art 3 mentioned above, the consideration was paid onto prevention of the dusts and/or gas components from adhering and/or deposing on the light emission surface of the laser ray of said wavelength converter element and/or the light receiving surface of said optical member for separation of the laser ray, by cutting off the portion defined between the wavelength converter element and the laser beam separation optical member from the outside, however no consideration was made upon prevention of adhesion or attaching of contaminating materials (contaminants) onto the optical resonator as a whole, including such the non-linear optical crystal, etc.

As explained in the above, any one of those prior arts 1 to 4 pays the consideration upon prevention of adhesion or attaching of the contaminants onto the optical resonator, as a whole, including the non-linear optical crystal, etc., with simplified construction thereof, but without receiving the ill influence so much from the control of increasing temperature of the non-linear optical element (i.e., the non-linear optical crystal).

An object of the present invention is, for dissolving such the problem(s) as mentioned above, to provide an ultraviolet laser-generating device, being simple in the structure thereof and able to convert the laser ray entered into with superior efficiency, with preventing adhesion or attaching of the contaminants on the whole optical resonator, including the non-linear optical crystal, etc., but without receiving the ill influence so much from the heat generated by the non-linear optical element, in particular, in the wavelength converter thereof, without decrease in intensity of an output of the ultraviolet laser ray, while obtaining a long lifetime thereof.

Also, other object of the present invention is to provide an ultraviolet laser-generating device and a maintenance method therefor, wherein an investigation can be made on a cause in the wavelength converter, when occurring the decrease in intensity of an output of the ultraviolet laser ray, thereby enabling to perform the maintenance thereof with ease.

Further, other object of the present invention is to provide a defect inspection apparatus and a method thereof, with using such the ultraviolet laser-generating device mentioned above, wherein microscopic test pattern formed on an object to be examined, such as the semiconductor wafer, etc., with an aid of illumination of stable intensity obtained by the ultraviolet laser ray, thereby enabling to examine the defects in the microscopic test patterns on the test object.

Also, further other object of the present invention is to provide a detect inspection apparatus and a method thereof, for achieving a long lifetime therewith, while can be maintained easily.

For achieving the above object(s) mentioned in the above, according to the present invention, in the ultraviolet laser-generating device, with paying an attention onto suppression upon potential of generating chemical gas reacted with residual organic matters, by irradiation of the ultraviolet laser ray within an optical resonator of the wavelength converter, the optical resonator is so constructed that no residual organic matter floats therein. In more details, the optical resonator and the non-linear optical element are provided within a container, hermetically, while replacing an inside of the container by an inert gas under the condition of preventing the organic matters from entering from an outside, so as to provide an environment where oxidation is reluctant to occur therein, as well as to prevent the heat due to isothermal control of the non-linear optical element from filling up therein, thereby preventing the ill influence of the heat upon other optical elements.

Namely, for accomplishing the above object(s), first of all, according to the present invention, there is provided an ultraviolet laser-generating device, comprising:

a laser ray source for irradiating and emitting a basic wave of laser ray therefrom;

a wavelength converter device for receiving the basic wave of laser ray emitted from said laser ray source and for converting it into an ultraviolet laser ray composed of a multiplied high harmonic light of the basic wave of laser ray; and a container having an inlet window, upon which the basic wave of laser ray emitted from said laser ray source is incident upon, and an outlet window for emitting the ultraviolet laser ray composed of the multiplied high harmonic light of the basic wave of laser ray, and installing said wavelength converter device therein, wherein said container is filled up with an inert gas therein.

Also, according to the present invention, there is provided the ultraviolet laser-generating device, as defined in the above, wherein said wavelength converter device comprises:

an optic resonator, being located within said container and constructed with plural optical members, for resonating the basic wave of laser ray; and a non-linear optical element, being located within said container and constructed with plural optical members, for generating the ultraviolet laser ray composed of the multiplied high harmonic light obtained from the basic wave of laser ray.

Also, according to the present invention, there is provided the ultraviolet laser-generating device, as defined in the above, wherein said container is hermetically sealed, and is further provided with means for discharging residual gas within said container and means for supplying the inert gas into said container.

Also, according to the present invention, there is provided the ultraviolet laser-generating device, as defined in the above, wherein on a part of inner wall of said container is provided trap means for fixing contaminants floating within said container thereon.

Also, according to the present invention, there is provided the ultraviolet laser-generating device, as defined in the above, wherein said container, in which said wavelength converter device is installed, is constructed in dual or triple construction, for defining an aperture between them, to be filled up with the inert gas therein.

Also, according to the present invention, there is provided the ultraviolet laser-generating device, as defined in the above, further comprising an optical detection means for detecting contamination condition within said container.

Also, according to the present invention, there is provided the ultraviolet laser-generating device, as defined in the above, wherein said optical detection means comprises plural number of photoelectric conversion elements positioned within said container.

Also, according to the present invention, there is provided the ultraviolet laser-generating device, as defined in the above, further comprising a detection means for detecting an output intensity of the ultraviolet laser ray emitted from said wavelength converter device.

Also, according to the present invention, there is provided the ultraviolet laser-generating device, as defined in the above, wherein said laser ray source comprises a solid-state laser-generating device.

Also, according to the present invention, there is provided the ultraviolet laser-generating device, as defined in the above, wherein said laser ray source comprises a Nd:YAG laser and a wavelength converter for converting the laser ray from said Nd:YAG laser into a laser ray having ½ wavelength thereof.

According to the present invention, for accomplishing the above object(s), there is further provided a defect inspection apparatus for detecting defects in microscopic patterns formed on a test object, with using an ultraviolet laser ray, comprising:

an ultraviolet laser-generating device;

an illumination optical system for irradiating the ultraviolet laser ray emitted from said ultraviolet laser-generating device upon the test object;

an optical system for forming an optical image obtained from said test object, being illuminated by said illumination optical system;

a photoelectric converter for converting the optical image, which is formed by said optical system, into a signal upon receipt thereof; and a defect detection circuit for detecting the defect on said test object upon basis of the signal obtained from said photoelectric converter.

Moreover, according to the present invention, for accomplishing the above object(s), there is also provided a defect inspection apparatus for detecting defects in microscopic patterns formed on a test object, with using an ultraviolet laser ray, comprising:

a plurality of ultraviolet laser-generating devices, being aligned so that the ultraviolet laser rays emitted are on a same axis;

an illumination optical system for irradiating the ultraviolet laser ray(s) emitted from at least one or more of said ultraviolet laser-generating devices upon the test object;

an optical system for forming an optical image obtained from said test object, being illuminated by said illumination optical system;

a photoelectric converter for converting the optical image, which is formed by said optical system, into a signal upon receipt thereof; and a defect detection circuit for detecting the defect on said test object upon basis of the signal obtained from said photoelectric converter.

Also, according to the present invention, there is provided the ultraviolet laser-generating device, as defined in the above, wherein at least one of said plurality of ultraviolet laser-generating devices is for a spare.

Also, according to the present invention, there is provided the ultraviolet laser-generating device, as defined in the above, wherein said illumination optical system comprises an optical system for combining the ultraviolet laser rays emitted from each of said plurality of ultraviolet laser-generating devices, to illuminate the test object therewith.

Also, according to the present invention, there is provided the ultraviolet laser-generating device, as defined in the above, wherein said illumination optical system comprises a coherence reduction optical system.

Furthermore, according to the present invention, for accomplishing the above object(s), there is provided a method for inspecting defects in microscopic patterns formed on a test object, with using an ultraviolet laser ray, comprising the following steps:

generating an ultraviolet laser ray by the ultraviolet laser-generating device;

illuminating the test object with using the ultraviolet laser ray generated by said generating step;

forming an optical image of the test object from light obtained in said illumination step of the test object;

converting the optical image obtained in said forming step into a signal upon receipt thereof; and detecting the defect on said test object upon basis of the signal obtained in said converting step.

Furthermore, according to the present invention, for accomplishing the above object(s), there is provided a method for inspecting defects in microscopic patterns formed on a test object, with using an ultraviolet laser ray, comprising the following steps:

generating a plurality of ultraviolet laser rays, so as to be aligned with on a same axis, as one ultraviolet laser ray;

illuminating the test object with using the one ultraviolet laser ray aligned in ed said generating step;

forming an optical image of the test object from light obtained in said illumination step of the test object;

converting the optical image obtained in said forming step into a signal upon receipt thereof; and detecting the defect on said test object upon basis of the signal obtained in said converting step.

And, according to the present invention, for accomplishing the above object(s), there is also provided a method for maintaining the ultraviolet laser-generating apparatus as defined in the claim 8, comprising the following steps:

monitoring an output of the output intensity detecting means for comparing it to a certain value;

obtaining an output of said optical detection means for detecting contamination condition within said container of the ultraviolet laser-generating apparatus; and determining maintenance of the ultraviolet laser-generating apparatus, upon basis of an output obtained by said obtaining step.

DETAILED DESCRIPTION OF PREFERRED EMBODIMENT(S)

Figure 1:
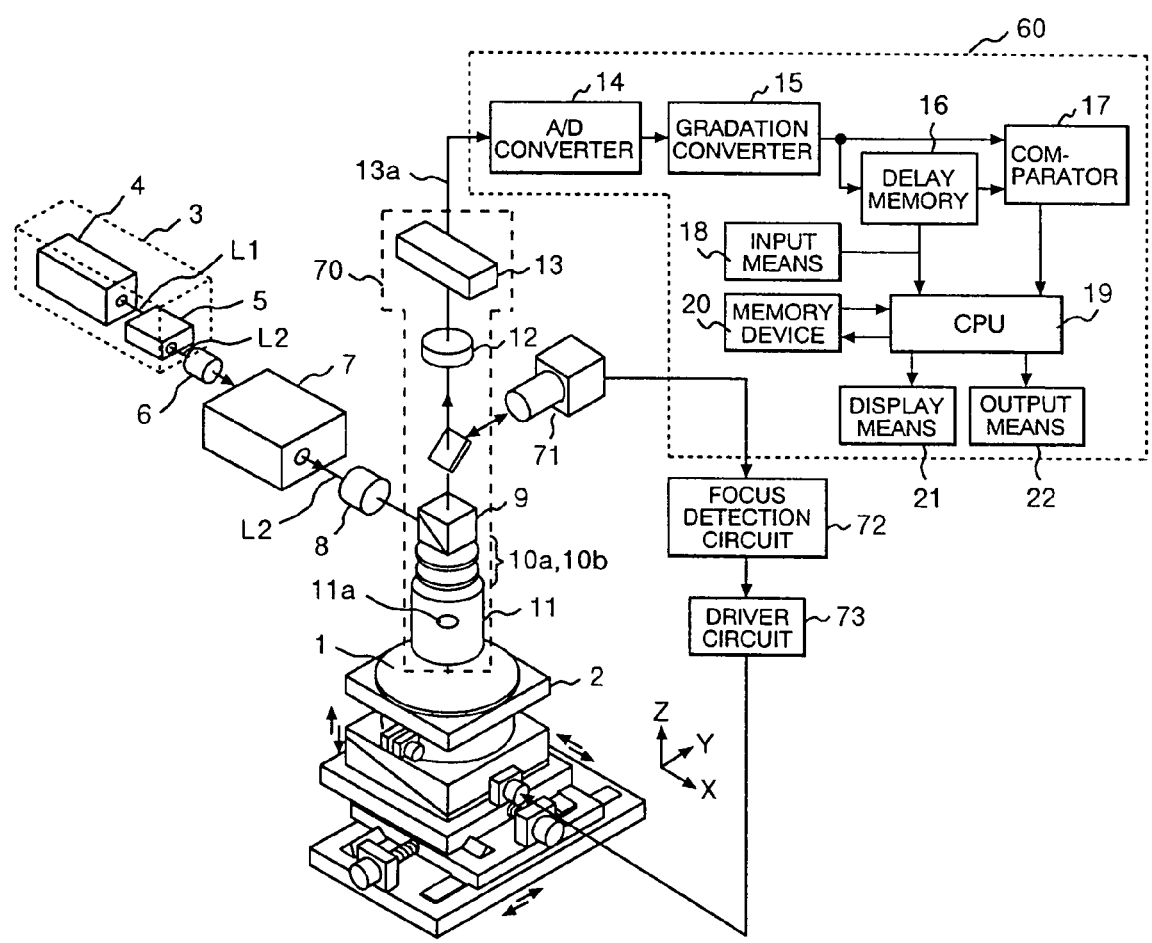
FIG. 1 shows the construction of a defect inspection apparatus as a first embodiment, according to the present invention.

Hereinafter, explanation will be given on embodiments of a high-resolution optical system, a defect examining apparatus and a method thereof, with using such the optical system therein, according to the present invention, by referring to the attached FIGS. 1 to 20.

First, explanation will be given on a first embodiment of the defect examining apparatus according to the present invention. According to the present invention, for the purpose of obtaining high-brightness illumination in DUV (Deep Ultraviolet) region, a device for emitting an ultraviolet laser ray therefrom is applied as a light source (i.e., a source of ultraviolet laser ray) 3. A stage 2 has freedom in the directions of X, Y, Z and θ, on which as a sample 1 is mounted a semiconductor wafer (an object to be tested: test object), for an example, on which is formed patterns to be tested (test patterns). The ultraviolet laser ray (DUV laser ray) L2, which is emitted from the source 3 of ultraviolet laser ray, through a beam expander 6, an optical system 7 provided for the purpose of coherence reduction, a lens 8, a polarization light splitter 9, and a group 10 of polarizer elements, is incident upon an objective lens 11, to be irradiated upon the object to be tested (for example, the semiconductor wafer: test object) 1, on which is formed the test pattern. The beam expander 6 is provided for expanding the ultraviolet laser ray up to a certain size thereof, and it is in a form of so-called the Koehler illumination, i.e., it is irradiated upon the sample 1 after being condensed in the vicinity of the pupil 11a of the objective lens 11 by means of the lens 8.

Figure 20:
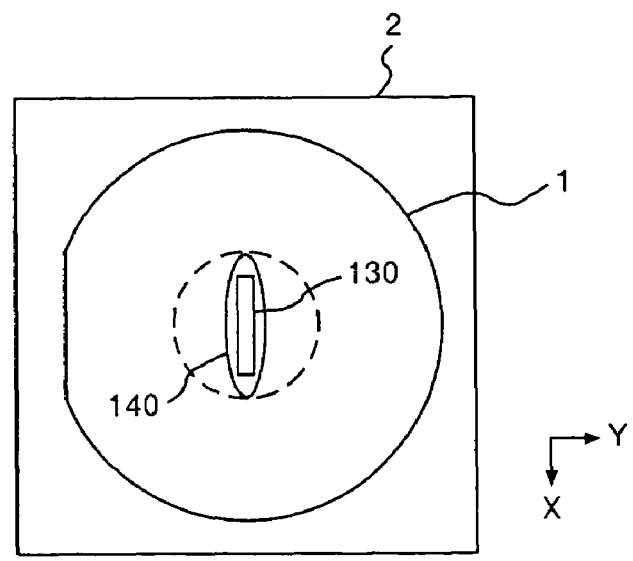
FIG. 20 is a view for showing luminous flux for slit illumination used in case of applying a TDI sensor as an image sensor.

The reflection light, or an optical image obtained from the sample 1 is detected, through the objective lens 11, the group 10 of polarizer elements, the polarization light splitter 9 and further an image-forming lens 12, by a image sensor 13, from the upper direction of the sample 1. For the image sensor 13, it is necessary to detect the DUV light and it may be constructed by, such as, a TDI (Time Delayed Image) sensor. In case of applying the TDI sensor as such the image sensor 13, as shown in FIG. 20, it is preferable to construct the lens 8 to include a cylindrical lens 8 therein, so as to bring the luminous flux for illumination upon a slit form 140 fitting to the light receiving surface 130 of the TDI sensor, from a view point of an efficiency of the illumination.

Figure 11:
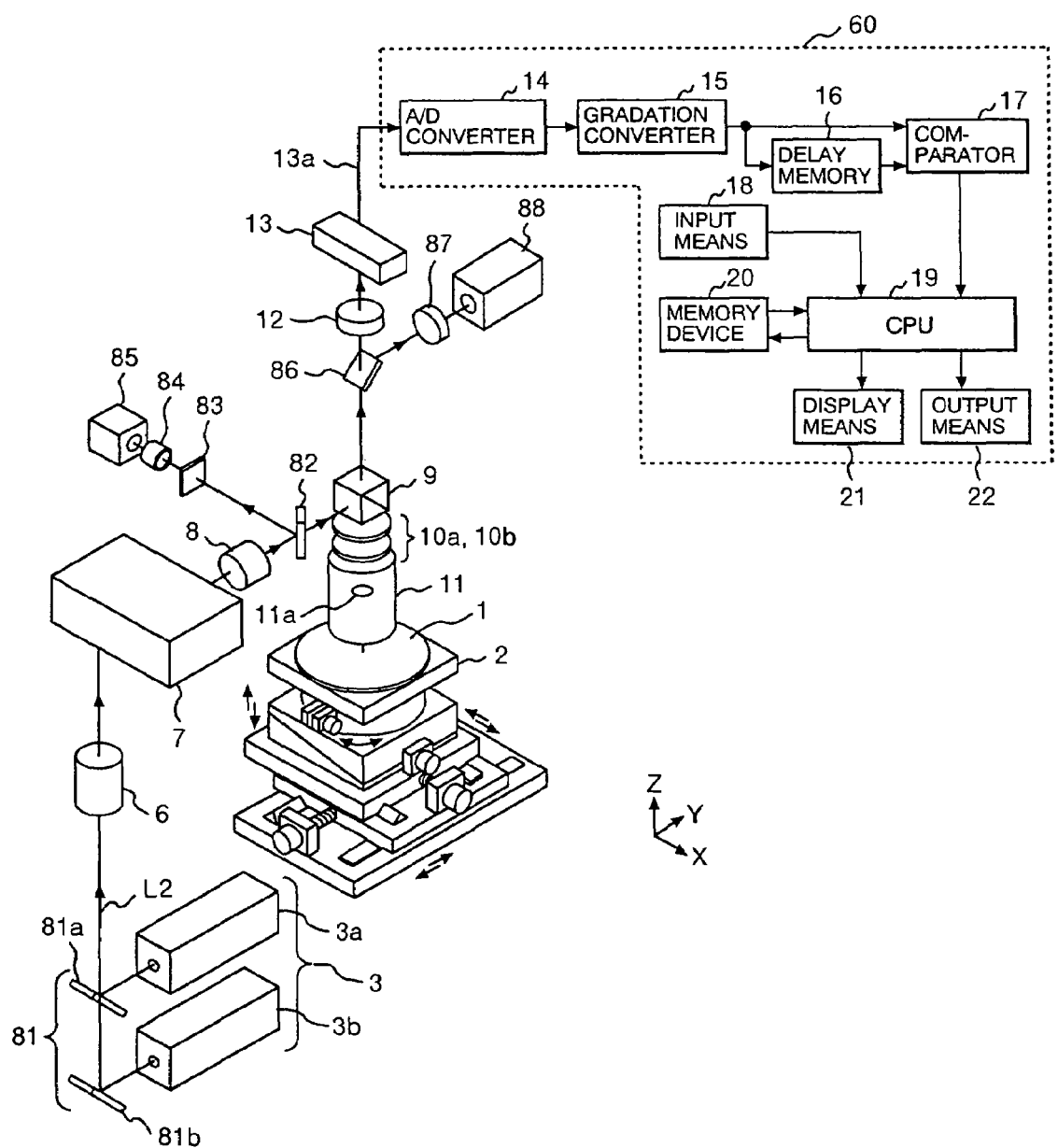
FIG. 11 is the structure view of showing a second embodiment of the defect examination apparatus, according to the present invention.

The polarization light splitter 9 has a function of reflecting the laser ray when the polarization direction thereof is in parallel with the reflection surface, while penetrating it when that is perpendicular thereto. The ultraviolet laser ray generated by the ultraviolet laser ray source 3 is inherently a polarization laser ray, and the polarization light splitter 9 is so positioned that the ultraviolet laser ray L2 emitted from the coherence reduction optical system 7 is reflected by the total reflection thereon. The test patterns formed on the test object 1, such as the wafer, in process, show various shapes or configurations, therefore the reflection light from the patterns has various polarization directions. The group 10 of polarizer elements, controlling the laser illumination ray and the reflection light, has a function of adjusting the rate of polarization in the illumination light, so that the reflection light does not reach upon the image sensor 13 accompanying with unevenness in brightness due to the shapes of the patterns and the difference in density thereof. For example, there are installed a ½ wavelength plate 10a and ¼ wavelength plate 10b for shifting the phase of the illumination light by 45 degree to 90 degree. Therefore, the light irradiating from the group 10 of polarizer elements upon the test object 1 for illumination comes to be the light that is polarized circularly, and thereafter, all the lights reflected (or scattered) upon the test object 1, once polarized by the group 10 of polarizer elements, are further polarized by 90 degree thereby in the direction of the polarization thereof on the reflection surface, then they penetrate through the polarization beam splitter 9. In this manner, since the resolution of the optical system 70 can be changed depending upon the condition on the illumination, or the condition on polarization of the detection light. Therefore, it is possible to improve the performance (i.e., the resolution) of the optical system 70 through detecting the reflection light, changing depending upon the density of the circuit patterns formed on the test object 1, by means of the image sensor 13, while controlling the polarization condition thereof, by controlling the polarization elements 10a and 10b to rotate around the optical axes thereof, relatively, upon basis of a spatial image of a plane of pupil of the objective lens 11, which is detected by a mirror 86, a lens 87 and a detector 88, as shown in FIG. 11 which will be explained later, for example.

And, the image sensor 13 is formed by a sensor of, such as an accumulation type, which can detect the ultraviolet lays (i.e., the TDI sensor), for example, thereby outputting an image signal of light and shade corresponding to the brightness (i.e., the light and shade) of reflection light from the test patterns which are formed on the test object 1. Namely, scanning the stage 2 while moving the test object 1 at a constant speed, the image sensor 13 detects information of the brightness (the light and shade image signal) of the test patterns that are formed on the test object 1. And the light and shade image signal 13a obtained from the image sensor 13 is inputted into a signal processing circuit 60, in which the inspection on defects is conducted, including the foreign matters in/on the test object. The signal processing circuit 60 may be constructed with an A/D converter 14, a gradation converter 15, a delay memory 16, a comparator 17, a CPU 19, etc. Further, the A/D converter 14 converts the light and shade image signal 13a obtained from the image sensor 13 into a digital image signal.

An optical system 71 for focus detection detects the deviation of the stage 2 in the Z direction. And, a circuit 72 for focus detection, processing the deviation of the stage 2 in the Z direction detected by the focus detection system 71, controls driving of deviation of the stage 2 in the Z direction, for example, upon the basis of a drive control instruction from a driver circuit 73 which corresponds to that processing. Due to this, it is possible for the image sensor 13 to detect the brightness information of the test patterns formed on the test object 1 under the condition of focusing thereupon, with high accuracy.

The gradation converter 15 may be constructed with, for example, an eight (8) bit gradation converter, and it treats the gradation conversion, as shown in Japanese Patent Laying-Open No. Hei 8-320294 (1996), upon the digital image signal that is outputted from the A/D converter 14. Namely, the gradation converter 15 performs conversion into a logarithm, an exponent, a polynomial, etc., so as to make compensation for a thin film that is formed on the test object 1, such as the semiconductor wafer, etc., in process, as well as for the unevenness in brightness of the image produced by interference of the laser light.

The delay memory 16 is provided for delaying an output of image signal from the gradation converter 15 by the scanning a width of the image sensor 13, through memorizing it in an amount for one (1) cell, one (1) chip or one (1) shot, which construct the test object 1, such as the semiconductor wafer, etc.

The comparator 17 is for comparing the image signal outputted from the gradation converter 15 and the image signal obtained from the delay memory 16, so as to detect a portion(s) being inconsistent with, as the defect(s). Namely, the comparator 17 compares, in more details, the image delayed by the amount corresponding to a cell pitch, etc., which is outputted from the delay memory 16, and the detected image. Accordingly, inputting the coordinates, for example, arranged data on the test object 1, such as the semiconductor wafer, obtainable upon the basis of design information, with using an input means 18 which may be constructed with a keyboard, a recording medium, a network, etc., the CPU 19 produces defect inspection data upon basis of the comparison result in the comparator 17, so as to store it into a memory device 20. This defect inspection data can be displayed on a display means 21, such as a display, etc., or may be outputted to an output means 22, thereby enabling observation of a spot(s) of defects through other review device, etc.

Further, the details of the comparator 17 may be constructed with, as shown in Japanese Patent Laying-Open No. Sho 61-212708 (1986), for example, a circuit for adjusting positions on images, a circuit for detecting difference between the adjusted images, an inconsistency detector circuit for binary-coding the difference of image, and a character extraction circuit for extracting an area, a length, coordinates, etc., from the binary-coded output.

Next, explanation will be explained on an embodiment of the source of ultraviolet laser ray (i.e., the ultraviolet laser-generating device). For obtaining high resolution, there is a necessity of shortening the wavelength of light, and for improving the test speed, the illumination of high brightness. Conventionally, a discharge lamp of mercury-xenon is used, and it is used widely in the visible region of the light emission spectrums (i.e., the emission line spectrums) that the lamp generates. However, separating from those light intensities, the emission line spectrums in the ultraviolet and the deep ultraviolet regions come up only around several %, comparing to that of the visible light (i.e., that in the visible light regions), a large-scaled light source is necessary for obtaining a desired brightness with certainty. In case of such the large-scaled light source, there is a limit to separate it from the optical system for protection from the ill influence of heat generation thereof. From this viewpoint, according to the present invention, the ultraviolet laser beam (DUV (Deep Ultraviolet) ray) is generated by means of the light source 3. The ultraviolet laser ray indicates the laser ray from 100 nm to 400 nm in wavelength, and the DUV laser ray is the laser ray from 100 nm to 314 in wavelength.

Figure 2:
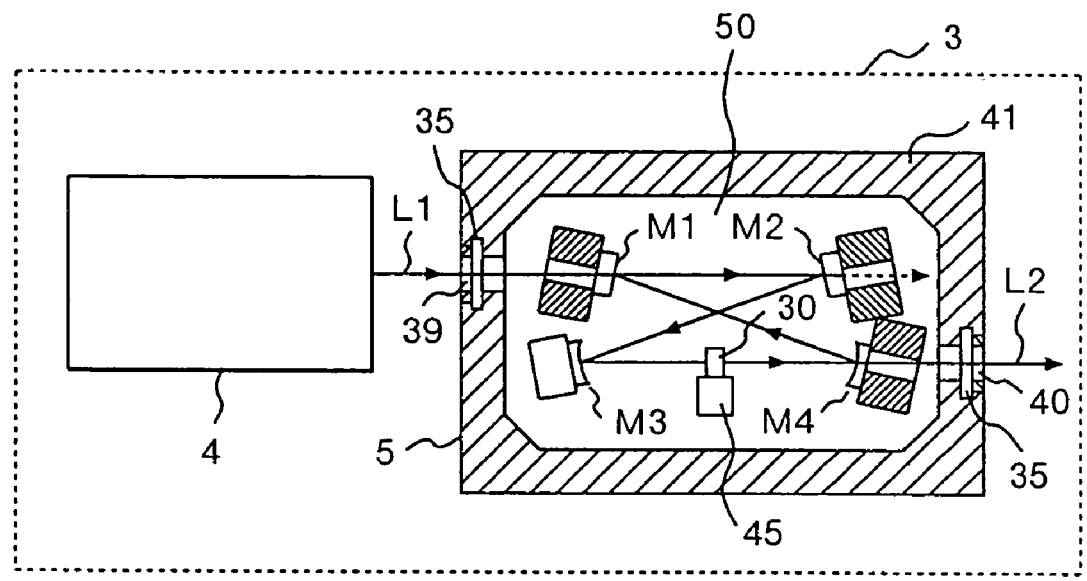
FIG. 2 shows the outline structure of an ultraviolet laser-generating device, according to the present invention.

The ultraviolet laser ray source (the ultraviolet laser-generating device) 3 is constructed with, as shown in FIG. 2, a solid-state laser device (a laser excitation light source) 4 for emitting a basic wave of laser ray of 532 nm in wavelength, and a wavelength converter device 5, for example. The solid-state laser device 4, penetrating Nd:YAG laser ray of 1064 nm in wavelength through a non-linear optical crystal thereof, so as to obtain a wave doubled in frequency (½ in wavelength), is so controlled that it emits the laser ray of 532 nm in wavelength at a constant intensity. Namely, the solid-state laser device 4 for outputting the doubled wave of the Nd:YAG laser ray is so constructed that it controls current of a laser power source depending upon a monitor output, thereby to emit an output of the laser ray L1 having a constant intensity. The laser ray L1 of wavelength 532 nm emitted from the solid-state laser device 4 is in the single mode oscillation, and is incident upon the wavelength converter device 5.

Also, it does not matter whether the oscillation of the solid-state laser device 4 as the ultraviolet laser ray source 3 is in a continuous oscillation mode or in a pulse oscillation mode, however in particular, in case of detecting the image from the test object 1 while continuously scanning the stage 2, that continuous oscillation is preferable.

Also, the ultraviolet laser ray source 3 may be constructed so that it converts the laser ray of the solid-state YAG laser (1064 nm) by the non-linear optical crystal, etc., thereby to generate the third ($3^{rd}$) high harmonic (355 nm) or the fourth ($4^{th}$) high harmonic (266 nm) of the basic wave thereof. Further, the ultraviolet laser ray source 3 may be constructed with a laser device of generating the laser ray having wavelength equal or less than 100 nm.

Next, explanation will be given on the wavelength converter device 5 as an element of the present invention. FIG. 2 is the view of the ultraviolet laser ray source 3 in the FIG. 1, seeing from the Z direction, for showing the outline structure (cross-section) of the wavelength converter device 5. Inside a container of the wavelength converter device 5, there are positioned mirrors M1 to M4. Being emitted from the solid-state laser-generating device 4 and incident upon a transparent window 35 at an entrance 39 provided on the container 41, the laser ray L1 passes through the mirror M1 and reaches the mirror M2. The mirror M2 penetrates through a part of the incident light, while it reflects the remaining thereof. The laser ray reflected upon the mirror M2 reaches to the mirror M3. A non-linear optical crystal 30 is disposed on an optical path between the mirror M3 and the mirror M4, and then the laser ray, being reflected upon the mirror M3 by the total reflection, passes though the non-linear optical crystal 30 to reaches the mirror M4. And, an optic resonator is constructed with such the optical members, each having high reflectivity, including those mirrors M1 to M4 therein. Further, the non-linear optical crystal 30 is disposed at a suitable location that can be calculated optically, therefore by means of this crystal 30, the incident light is converted into the second ($2^{nd}$) high harmonic of wavelength having wavelength of 266 nm. Upon the mirror M4, only the ultraviolet laser ray L2 of the second ($2^{nd}$) high harmonic passes through, therefore it is emitted outside the wavelength converter device 5, via the transparent window 35 at an exit 40, which is provided on the container 41. Namely, upon the mirror M4 is treated a coating, which penetrates through the second ($2^{nd}$) high harmonic but reflects other wavelengths. The laser ray L3 that is not converted by the non-linear optical crystal 30 is reflected upon the mirror M4 to reach the mirror M1, and it follows the same optical path for the laser ray L1, again. Herein, a portion of the incident light passing through the mirror M2 is detected by a detector means which is not shown in the figure, to detect the error between the frequency of the incident light and the resonance frequency of the wavelength converter, thereby bringing both into synchronism with (in a resonating condition), always. In more details, by means of a servo-mechanism not shown in the figure (for example, a piezoelectric element, etc.), the mirror M3 is moved minutely or finely, so that the length of the optic resonator is controlled with high accuracy. With controlling the length thereof in this manner, the optic resonator is constructed with the optical members, each having the high reflectivity, such as the mirrors M1 to M4. And, with the above-mentioned optic resonator and the non-linear optical crystal 30, which are provided inside the container 41, the wavelength converter 50 is constructed.

On a while, the ultraviolet laser ray L2 of wavelength 266 nm, which is emitted from the wavelength converter device 5, has coherence therewith, and it comes to be a cause of generating so-called speckles when illuminating the circuit patterns on the test object 1 with using such the laser ray. Accordingly, in the illumination with using such the ultraviolet laser ray L2, it is necessary to reduce the coherence. For reduction of the coherence, it is sufficient to reduce down either one of the time and spatial coherences thereof. Then, according to the present invention, only the special coherence is reduced down by means of an optical system 7 for reduction of the coherence.

Figure 3:
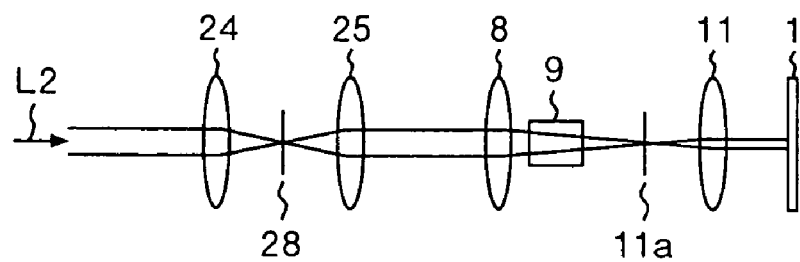
FIG. 3 is a diagram of showing an embodiment of an optical system for illumination, including an optical system for reducing coherence therein, as shown in the FIG. 1.

FIG. 3 is a block diagram for showing an embodiment of an illumination optical system, including the coherence reduction optical system 7 according to the present invention, therein. The laser ray L2 emitted from the transparent window 35 at the exit 40 of the wavelength converter device 5 is expanded in the beam expander 6 to a parallel luminous flux of a certain size, to be condensed at the focal position of the lens 24, and thereafter it is condensed upon the pupil 11a of the objective lens 11 through the lenses 25 and 8, and the polarization beam splitter 9, as well. However, the focal position 28 of the lens 24 is also that of the lens 25 at the same time, therefore the focal position 28 is in conjugated relation with the position of the pupil 11a of the objective lens 11.

Figure 4:
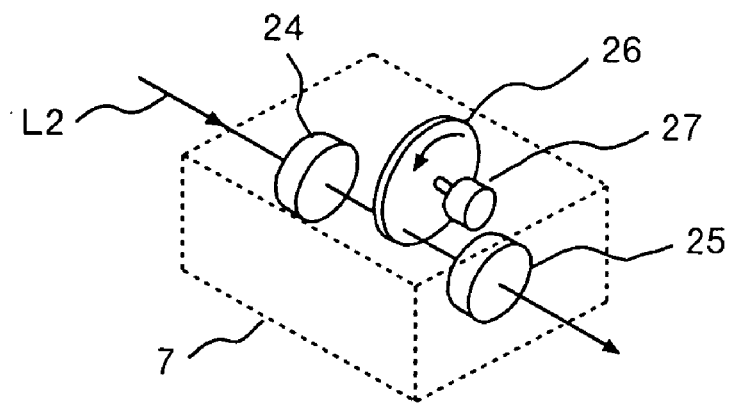
FIG. 4 is a perspective view of showing an embodiment of the optical system for reducing coherence therein.
Figure 5:
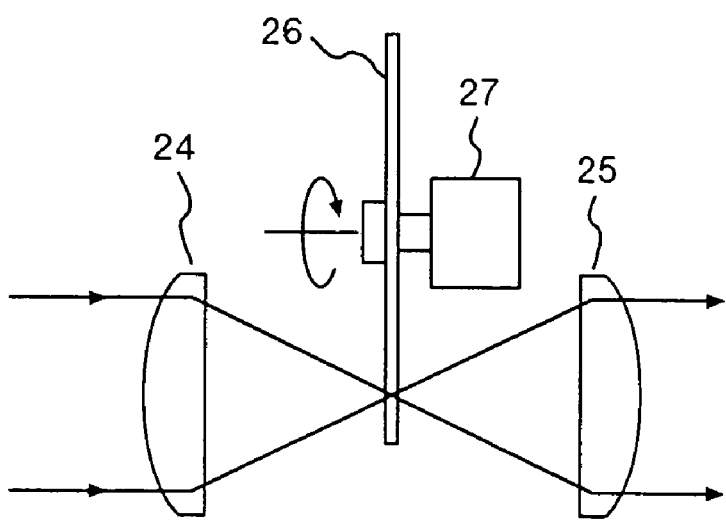
FIG. 5 is a front view of the optical system for reducing coherence therein, which is shown in the FIG. 4.

In the coherence reduction optical system 7, as is shown in FIG. 4, for example, a scattering plate 26 of disc form is positioned at the focal point 28 on the optical path, and is rotated at high speed by a motor 27. Namely, as is shown in FIG. 5, the scattering plate 26, on the surface of which is machined with appropriate roughness, is positioned at the focal position of the lens 24 (and the lens 25), and the laser spot condensed upon the pupil 11a of the objective lens 11 is scanned by means of rotation of the motor 27, thereby reducing the coherence, in particular the spatial coherence thereof. The laser ray is expanded by the scattering plate 26 to a certain degree, however the lens 25 is selected to have numerical aperture to cover it, and the detailed specifications of that scattering plate 26 are determined by experiments. Further, with the coherence reduction optical system 7, the manner for constructing thereof should not be restricted only to the above-mentioned, but it is also possible to apply a polyhedron rotation mirror, a vibrating rotation mirror, etc.

By the way, in the laser ray source 3 used for illumination, the ultraviolet ray of wavelength 266 nm is obtained by doubling the frequency of the excitation light L1 of wavelength 532 nm obtained from the solid-state laser, with using the mirrors M1 to M4 disposed within the container of the wavelength converter device 5 and the non-linear optical crystal 30 as well, thereby obtaining the ultraviolet light of wavelength 266 nm. However, as was mentioned previously, the interior of the container of the wavelength converter device 5 is very delicate, due to the fact, for example, that the optical system must be synchronized with so that the frequency of the incident light is always in the resonating condition with the resonance frequency of the wavelength converter 50, etc. Among those, the non-linear optical crystal 30 has deliquescence therewith and is apt to be easily damaged from moisture. Accordingly, for obtaining the ultraviolet laser ray with stability, the surfaces of the mirrors M1 to M4 and the non-linear optical crystal, which are provided within the optical resonator, must be always kept in a clean condition.

Also, for obtaining a constant ultraviolet laser ray from the wavelength converter 50 provided within the container of the wavelength converter device 5, a thermostatic device (not shown in the figure) is provided within a slight movement mechanism 45 for supporting the non-linear optical crystal 30.

Herein, in case where it is impossible to maintain the interior of the container of the wavelength converter device 5 in such the clean condition, the irradiation of the ultraviolet laser ray causes chemical reactions and the reactant adheres and harden upon the surfaces of the optical elements, in the inside thereof, thereby bringing about the decrease of intensity in an output of the ultraviolet laser ray. Then, it is possible to manage by shifting the irradiation position of the laser ray upon the crystal 30, little by little, when the output intensity of the ultraviolet laser ray is decreased down, however it takes a large amount of labor and times.

Figure 6:
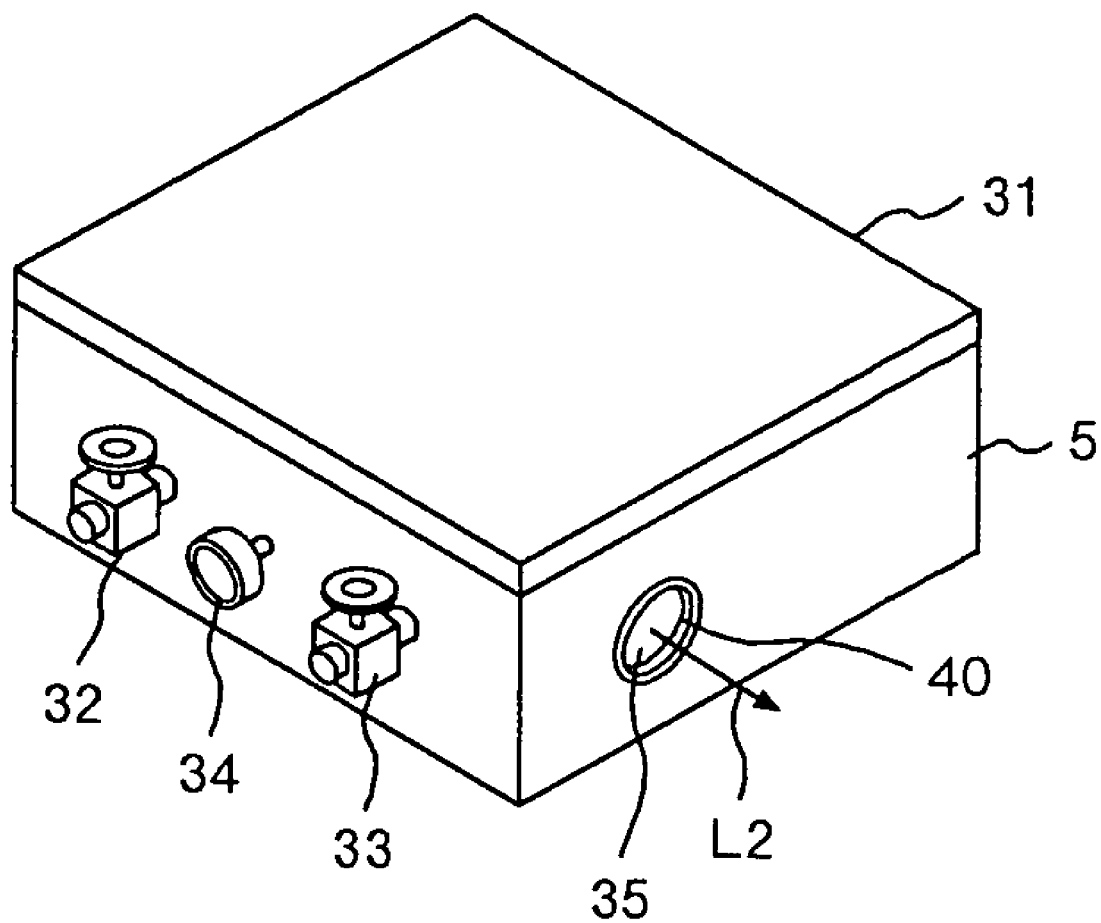
FIG. 6 is a perspective view of showing an outlook of a wavelength converter, according to the present invention.
Figure 7:
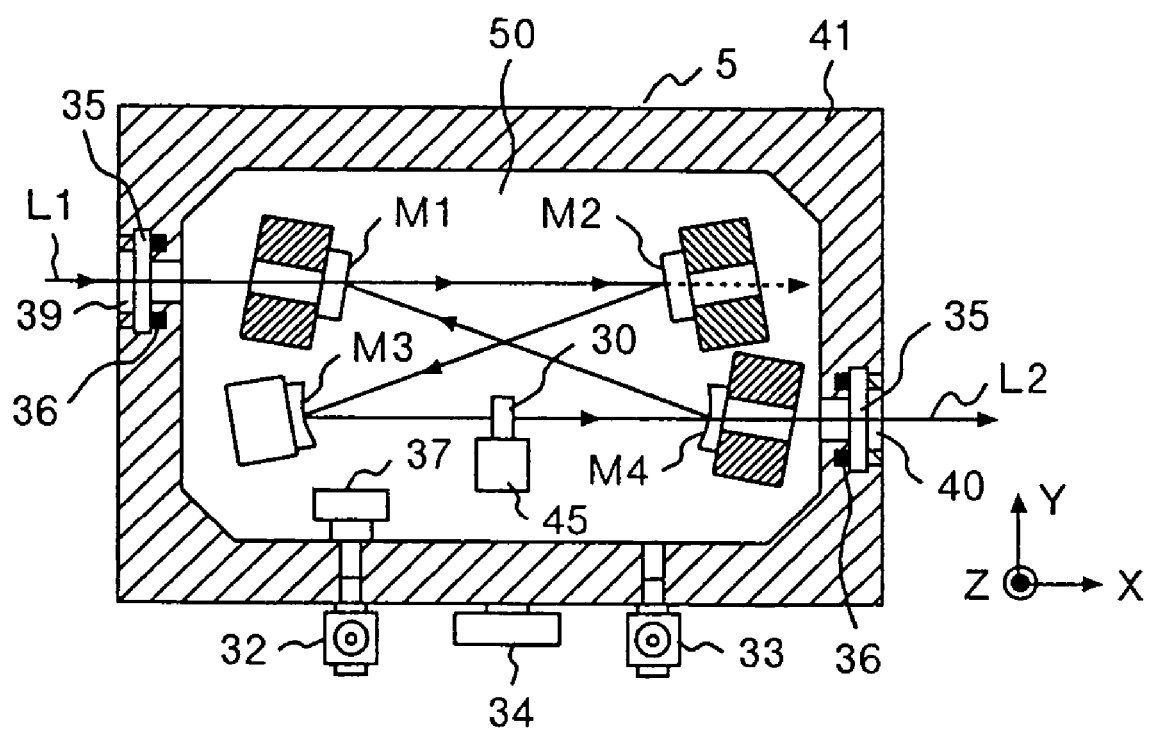
FIG. 7 is a cross-section view of showing a first embodiment of the wavelength converter, according to the present invention.

Then, first of all, explanation will be given on a first embodiment of the wavelength converter device 5. In this first embodiment, as shown in FIGS. 6 and 7, the wavelength converter 50, which is constructed with the optic resonator made with the optical members M1 to M4 and the non-linear optical crystal 30, is shut off or insulated from the air outside, by means of the container 41, i.e., within the construction of sealed condition. FIG. 7 shows the condition of removing a cover 31 therefrom. Namely, the transparent windows 35 are hermetically provided with using, such as an O ring 36, etc., at the inlet 39 and the outlet 40 for the laser ray, which are formed on the container 41. Further, on the container 41 are provided a supply valve 32, being provided with a filter 37 at a tip thereof, for supplying a gas for use of cleaning, such as an inert gas, from a gas reservoir (not shown in the figure) into the container 41, a discharge valve 33 connected to a discharge pump (not shown in the figure) for discharging residual gas within the container 41, and a detector 34 for observing the condition of the gas within the container 41, especially fulfillment of the inert gas therein. In this manner, the cleaning means for cleaning up the inside of the container 41 is constructed with, for example, the supply valve 32, connected to the inert gas reservoir (not shown in the figure) and provided the filter 37 at the tip thereof, the discharge valve 33 connected to the discharge pump, and the detector 34 for observing the fulfillment of the inert gas therein. Being constructed in this manner, as shown in the FIG. 6, after completion of the optical system therein, the container 41 of the wavelength converter device 5 is attached with the cover 31 thereon, and the discharge valve 33 thereof is connected to the discharge pump not shown in the figure, thereby discharging the residual gas in the container 41. Next, the inert gas is supplied from the supply valve 32 thereinto. The detector 34 may be a barometer, for example, for monitoring an atmospheric pressure within the container 41. The inert gas is preferably a gas that shows no chemical reaction with the laser ray within the wavelength converter 50, such as, nitrogen gas, argon gas, etc. Also, the filter 37 is provided at the tip of the supply valve 32, and this achieves functions of controlling the flow amount of the gas and preventing mixture of impurities therein, when supplying the inert gas through it.

In particular, under the condition where the residual gas in the container 41 is discharged by connecting the discharge valve (not shown in the figure) to the discharge pump 33, and next the inert gas is supplied from the supply valve 32 into the container 41, to be filled up therein at around one (1) atmospheric pressure, it is possible to close up the supply valve 32 and the discharge valve 33, thereby to bring the container 41 into a sealing up condition. And, after filling the inert gas from the supply valve 32 into the container 41 at around the one (1) atmospheric pressure, it is also possible to continue to run the inert gas at a very small amount, so that no fluctuation occurs in the laser ray.

According to the first embodiment mentioned in the above, it is possible to prevent the mixture of new foreign matters from coming into the container 41, and as a result, it is possible to maintain the surfaces of the mirrors M1 to M4 and the crystal 30, which are provided inside the optic resonator, always clean, thereby to prevent them from bringing about decrease of the ultraviolet laser ray in the output intensity thereof.

Figure 9:
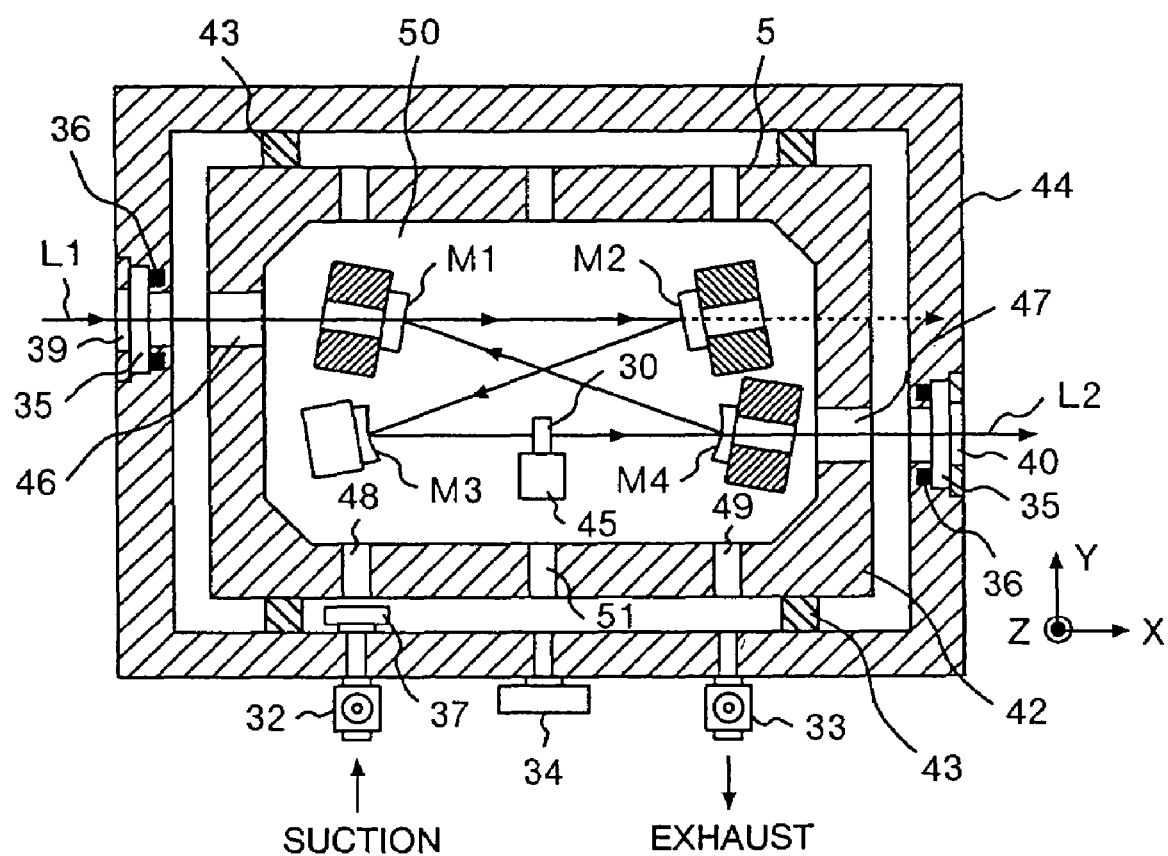
FIG. 9 is a cross-section view of showing a second embodiment of the wavelength converter, according to the present invention.

Next, explanation will be given on the second embodiment of the wavelength converter device 5 according to the present invention. In this second embodiment, as shown in FIG. 9, the wavelength converter 50 is shut off from the air outside, by means of dual structure, including the container 42 and a casing (container) 44, i.e., it has the structure in hermetically sealing condition. In the case of this second embodiment, it is possible to prevent the mechanical stress from being applied onto the wavelength converter 50 when closing the cover 31. Namely, on the outer casing 44, the transparent windows 35 are hermetically provided at the inlet 39 and the exit 40 with using, such as the O-rings 36, etc., and there are provided the valves 32 and 33 for supplying and discharging the gas and the detector 34 for observing the gas condition within the container. And, the container 42 building up the wavelength converter 50 therein is supported within the casing 44 by means of supporting members 43, thereby constructing the dual structure.

And, on the inner container 42, there are formed an inlet 46 for entering the incident laser ray through the transparent window 35 at the inlet 39, and an outlet 47 for emitting the ultraviolet laser ray L2 to the transparent window 35 at the outlet 40, and further are formed air suction openings 48 and air discharge openings 49 communicating between the inside and the outside of the container 42, as well as pressure openings 51. In particular, with provision of a large number of such the air suction openings 48 and the air discharge openings 49, being small in the size, they function as a buffer between the outside of the container 42 and the inside of the casing 44 even when continuing to run the very small amount of the inert gas, therefore it is possible to remove almost of flow of the inert gas within the container 42, i.e., remove fluctuation of the laser ray. Of course, under the condition where the residual gas in the container 45, including the container 42, is discharged therefrom by connecting the discharge valve (not shown in the figure) to the discharge pump 33, and next the inert gas is supplied from the supply valve 32 into the container 45, to be filled up with therein at around one (1) atmospheric pressure, it is possible to close up the discharge valve 33 and the supply valve 32, thereby to bring the container 45 into the sealing condition. In this manner, according to the second embodiment of the wavelength converter device 50, it is possible to prevent the stress from generating onto the wavelength converter 50, and also to prevent the container 42 from mixture of the new foreign matters, by supplying the inert gas of causing no chemical reaction with the laser ray, such as the nitrogen gas or argon gas, etc., to be filled up with therein. As a result of this, it is possible to keep the surfaces of the mirrors M1 to M4 and the crystal 30, which are provided inside the optic resonator, always in the clean condition, therefore it is possible to prevent them from bringing about the decrease in the output intensity of ultraviolet laser ray.

However, according to the second embodiment, the wavelength converter 50 is shut off from the air outside by means of the dual structure of the container 42 and the casing (container) 44, the container may be constructed with triple structure, although it comes to be complicated a little bit in the structure thereof. With such the triple structure of the container, since an aperture can be defined between the containers as the buffer, it is possible to remove the fluctuation of the laser ray, much more.

Figure 8:
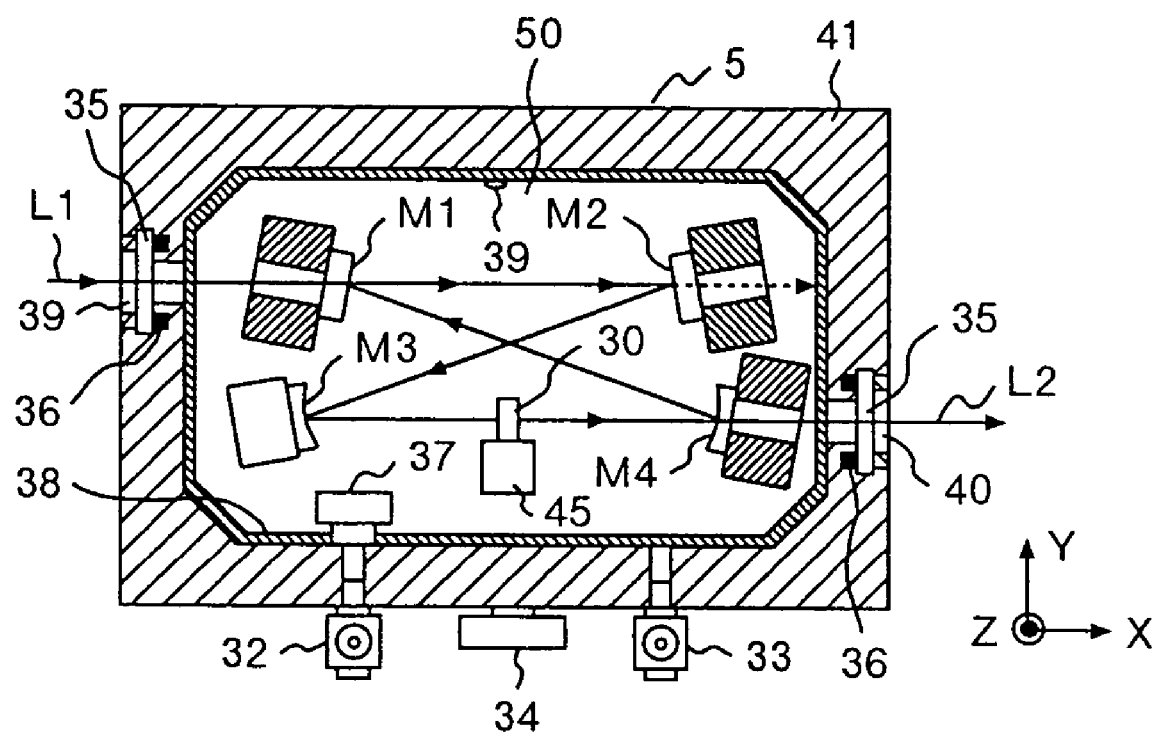
FIG. 8 is a cross-section view of showing a third embodiment of the wavelength converter, according to the present invention.

Next, explanation will be given on a third embodiment of the wavelength converter device 5 according to the present invention. This third embodiment, as shown in FIG. 8, is constructed by applying an adhesive or sticky material 38 (a trap means) on an inner wall of the container 41 of the first embodiment. Of course, the third embodiment may be constructed by applying the adhesive material 38 on an inner wall of the container 42 of the second one. According to this third embodiment, it is possible to prevent the foreign matter(s) 39, which stays within the container 42, from being blown up by wind pressure when supplying the inert gas therein, to adhere or attach upon the optical members inside. Further, according to this, it is also possible to catch the floating foreign matter(s) 39 touching on the adhesive material, when discharging the gas within the containers 41 (or 42) outside, thereby to hold it semi-permanently.

Figure 10:
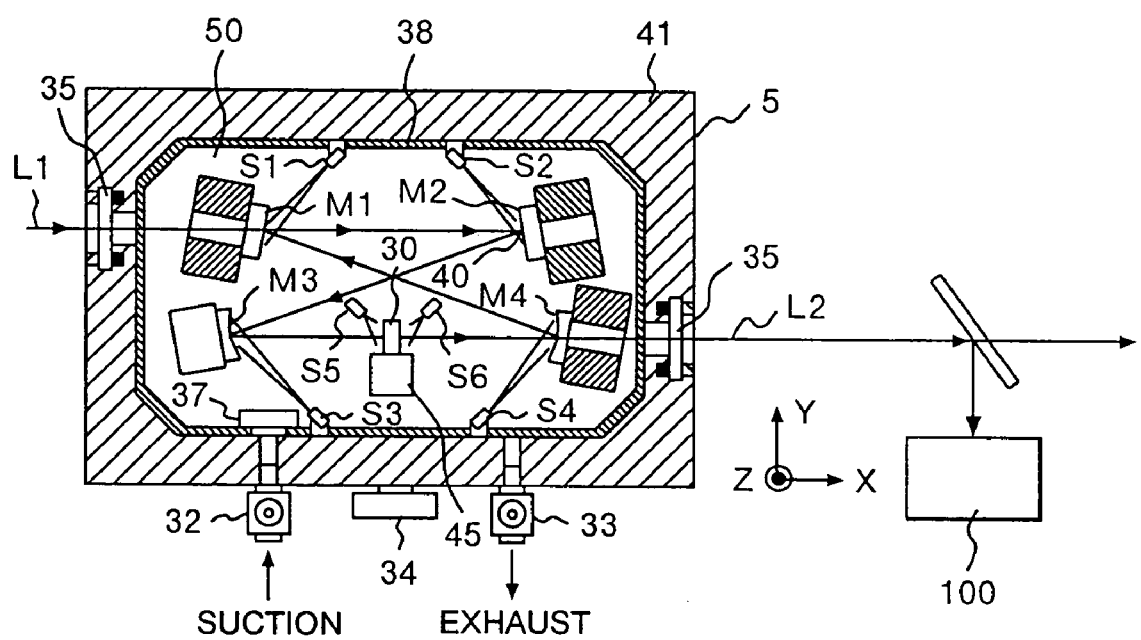
FIG. 10 is a cross-section view of showing a fourth embodiment of the wavelength converter, according to the present invention.

Next, explanation will be given on a fourth embodiment of the wavelength converter device 5, according to the present invention. In this fourth embodiment, as shown in FIG. 10, further a plural number of optic sensors S1 to S6 are positioned within the container of the wavelength converter device 5, in the third embodiment, and scattering light from the contaminant occurring within the container 41 (or 42) is detected by means of the plural number of the optic sensors S1 to S6, thereby detecting the degree of contamination, or the condition of contamination within the containers, in order to observe the contamination condition on the optical members M1 to M4, and on the non-linear optical crystal 30 as well. Namely, the plural number of those optic sensors S1 to S6 construct an optical contaminant detecting means for detecting the scattering light from the contaminant occurring within the container 41 (or 42). Since, ordinarily the contaminant is made of an organic matter, the optic sensors S1 to S6 detect the fluorescence scattering light generated by such the organic matter. And, each of the plural number of the optic sensors S1 to S6 is made from a light condensing lens and a photoelectric conversion element, and detects the contamination condition upon the surface of the mirror of M1 to M4 or the surface of the non-linear optical crystal 30, for example. Since the photoelectric conversion element generates electromotive force depending upon an amount of the receiving light thereon, a threshold value is provided for it, and then it can be decided that the surface(s) of the mirror(s) M1 to M4 and/or the surface of the non-linear optical crystal 30 is/are contaminated when it exceeds the threshold value. For example, it can be decided that the contaminant 40 adheres upon the surface of the mirror M2 if there is an output signal from the optic sensor S2. Since the wavelength of the laser ray is already known, it is possible to protect it from an ill influence of an external disturbed light, by applying the sensors having high sensitivity only a specific wavelength band as those sensors S1 to S6, and it is also possible to set the threshold value for detection to be low. Accordingly, even a very little contaminant can be detected upon the surfaces of the mirror M1 to M4 and the crystal 30, with high sensitivity. Monitoring the output of the ultraviolet laser ray L2 emitted from the wavelength converter device 5 by a detector means 100, which is constructed with the photoelectric conversion elements, etc., and which is provided separate from the optic path of the illumination light, an alarm can be given, for example, when decrease is found in the intensity thereof (for example, when it comes down to around 50% of an initial value), then the sensors S1 to S6 are determined by each, whether the output signal of which exceeds a threshold value predetermined for it or not. With this, a portion(s) which is/are contaminated with the contaminant(s) upon the surface(s) thereof can be specified or identified among the optical members, i.e., the mirrors M1 to M4 and the crystal 30. Then, the optical member(s), being determined contaminated, will be treated with cleaning upon the surface thereof, or will be replaced with a new or other optic member that in not contaminated.

However, as another method for monitoring the ultraviolet laser ray L2 emitted from the wavelength converter device 5, an output of the beam expander 6 or the coherence reduction optical system 7 may be monitored. Of course, when monitoring the output of the beam expander 6 or the coherence reduction optical system 7, the decrease in the output intensity due to the contamination of the optical system 6 or 7 is included into the output to be monitored.

Also, in a case where no output signal is produced from the optic sensors S1 to S6, and where the output intensity is reduced in the ultraviolet laser ray L2, which is emitted from the wavelength converter device 5, when monitoring it by the detection means as was mentioned in the above, the cause may be considered to lie in the non-linear optical crystal 30. In this case, a possibility is high that the inside of crystal 30 burns out upon the irradiation of the laser ray, therefore the non-linear optical crystal 30 may be adjusted to be shifted in the Y and Z directions by means of the slight movement mechanism 45, so that the ultraviolet laser ray L2 can be increased in the output intensity. Of course, the present fourth embodiment can be applied to the second embodiment shown in the FIG. 9, too.

As was explained in the above, with monitoring the contamination condition within the wavelength converter device, it is possible to make the determination upon the necessity of maintenance in the wavelength converter device, with ease and appropriateness, and as a result, it is possible to remove consumption of unnecessary or needless time paid for adjusting the optical system within the wavelength converter device without reasons.

According to the embodiments of the present invention mentioned in the above, it is possible to obtain a source of laser ray of a long life-time, without decrease of output intensity in the ultraviolet laser ray, i.e., stable oscillation of the ultraviolet laser ray for a long time period, by elongating the life-time of the wavelength converter. As a result of this, it is also possible to detect the microscopic patterns formed on the test object 1 with high resolution, thereby to examine those defects occurring in the microscopic patters with high reliability.

Next, a second embodiment of the detect examination apparatus, according to the present invention, will be explained by referring to FIGS. 11, 18 and 19. In this second embodiment, the difference from the first embodiment shown in the FIG. 1 lies in that, at first, as shown in FIGS. 19(a) and (b), the ultraviolet laser ray source (the ultraviolet laser-generating device) 3, each comprising the solid-state laser device (the laser exciting light source) 4 and the wavelength converter device 5, is provided in a plural number thereof so that the ultraviolet laser rays emitted from those ultraviolet laser ray sources 3 are on the same axle, and therefore as shown in the FIG. 19(b), they can be used by oscillating only one of them for exchanging it by the other(s) when the one is in trouble, or as shown in the FIG. 19(a), all of them are oscillated while operating each at the low output. Namely, in the second embodiment, the plural number of the ultraviolet laser ray sources 3a, 3b and 3c, each comprising the solid-state laser device 4 and the wavelength converter device 5 therein, are provided, and mirrors 81a, 81b and 81c are so constructed that the ultraviolet laser rays emitted from those ultraviolet laser ray sources 3a, 3b and 3c are reflected upon them on the same axle in a direction, such as of Z, so as to be inputted into the beam expander 6. In particular, as shown in the FIG. 19(b), selecting each of the mirrors 81a to 81c (a selection optical system) by exchanging (or shifting) thereof, it is possible to select the output(s) of the ultraviolet laser ray sources 3a to 3c. With this, it is possible to make the ultraviolet laser ray sources provided for spares emit the normal ultraviolet laser rays always, so as to irradiate upon the test object 1, to detect the microscopic patterns formed on that test object 1 with high resolution, and to detect the defects occurring in those microscopic patterns with high reliability. In this manner, even during a period when they are operating normally as the laser ray sources, it is possible to make adjustment on the wavelength converter device(s) 5 among them, being abnormal as the ultraviolet laser ray source, being broken or deteriorated therein, or to replace it/them by a normal wavelength converter device(s) 5 in place thereof.

However, as was shown in the FIG. 19(a), in a case where the ultraviolet laser rays emitted from the plural number of the ultraviolet laser ray sources 3a to 3c are applied upon a combining optical system of 81a to 81c to be combined with, it is possible to adjust an output automatically, by monitoring the output as a whole by, such as a TV camera 85, so that the current value is adjusted, for example, to be supplied to the solid-state laser device 4, which is included in the normal ultraviolet laser ray source(s) other than the deteriorated one, to increase the output thereof, thereby obtaining the monitored output as a whole at a predetermined value. And, for the wavelength converter device 5 of the deteriorated ultraviolet laser ray source, it is also possible to adjust the output intensity of the ultraviolet laser ray L2 so as to increase, through shifting the non-linear optical crystal 30 in the Y and Z directions by means of the slight movement mechanism 45.

Figure 18:
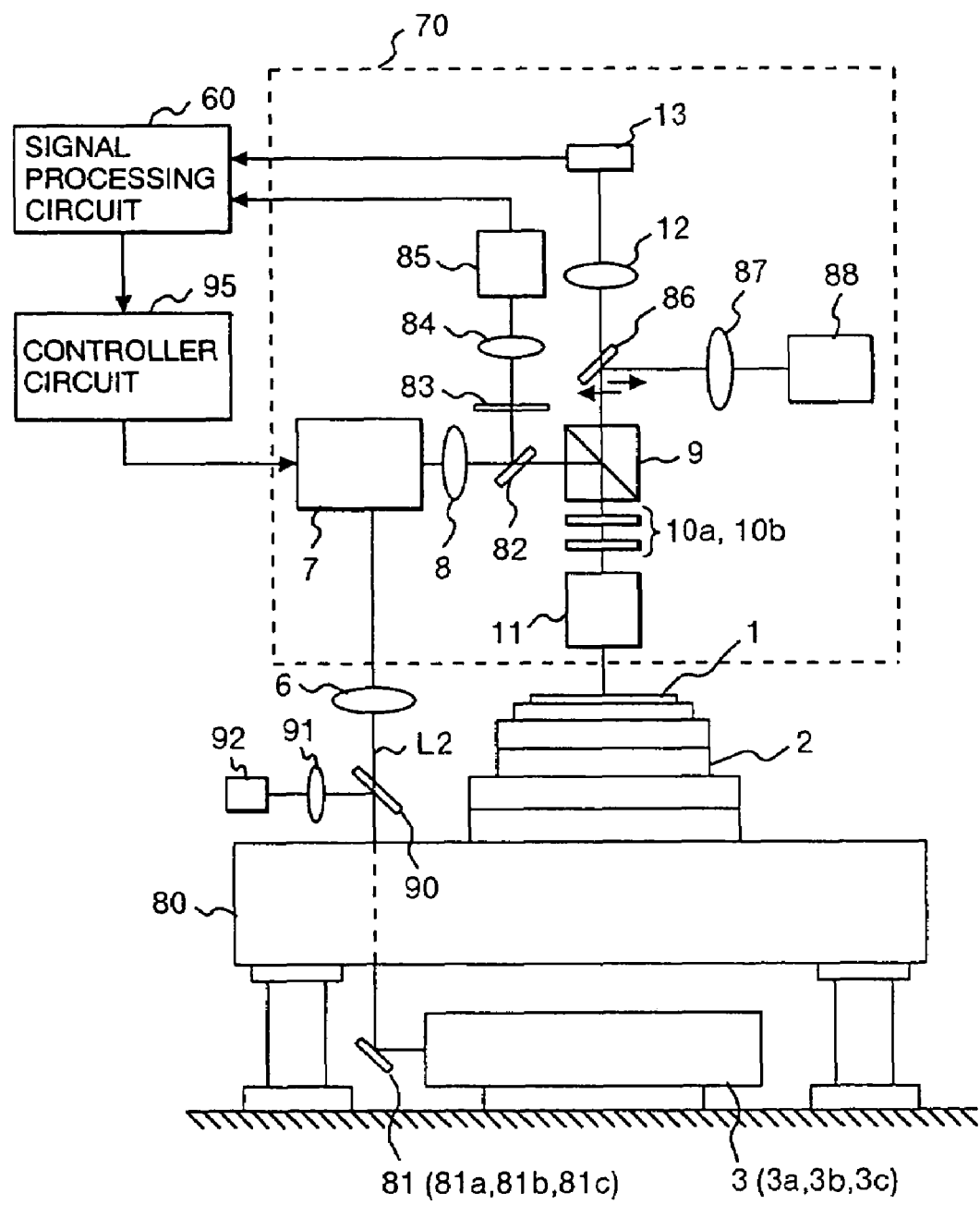
FIG. 18 is a front view of showing a second embodiment of the defect examination apparatus, according to the present invention.
Figure 19A:
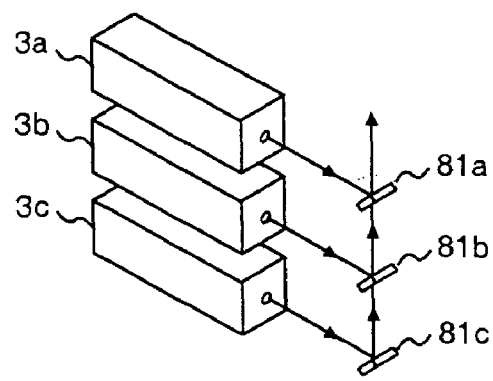
FIGS. 19(a) and (b) are views for explaining light sources of the ultraviolet laser beam used in the second embodiment, according to the present invention.
Figure 19B:
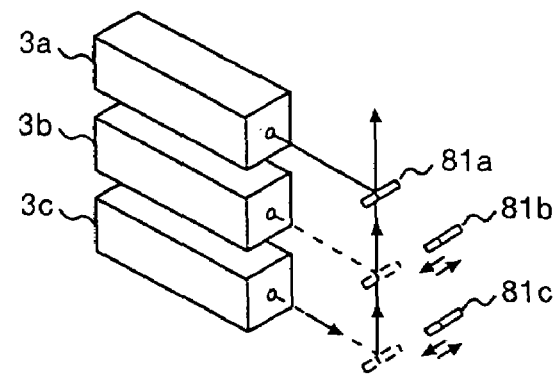

Further, as shown in the FIG. 18, with positioning the ultraviolet laser ray source 3 comprising plural light sources 3a and 3b separate from the optical system 70, it is so constructed that propagation of mechanical vibration generated by the stage, etc., and transmission of heat can be shut off from the ultraviolet laser ray source 3 to the optical system 7'Further, according to the present embodiment shown in the FIG. 18, the ultraviolet laser ray source 3 is provided under a base 80 for removing vibration. In this case, it is constructed to make exhaustion of the air locally, so that, not shown in the figure, the heat generated by the ultraviolet laser ray source 3 will not transmitted up to the upper portion of the base 80. The laser rays L2, each being emitted from the respective ultraviolet laser ray sources 3a to 3c, are reflected into the direction Z upon the mirrors 81a to 81c, respectively, and reach to the optical system 70 through a mirror 90 and the beam expander 6. In the pattern inspection thereof, the examination is conducted upon the whole surface of the semiconductor wafer 1 by scanning the stage 2, on which the wafer 1 is mounted, into the X and Y directions, however since the position of center of gravity of the stage is shifted accompanying with the movement thereof, the base 80 is inclined. In this case, the base 80 is turned back to the horizontal condition by means of an air turbo, etc., however since the ultraviolet laser ray L2 emitted from the ultraviolet laser ray source 3 is equal or less than 1 mm in a beam diameter, it can be expected that the optical axis of the optical system 70 comes out of that of the ultraviolet laser ray L2, temporally. Because of this, according to the present invention, the mirror 90, the lens 91, and a position detector 90 as well, are provided on the base 80, thereby detecting a shift amount of the ultraviolet laser ray L2, so as to shift the mirror 81 by an actuator, such as a piezoelectric element, etc., and to correct the optical path of the ultraviolet laser ray L2 being out of the axis thereof, at high speed. Herein, on the mirror 90 is coated a reflection film so as to reflect a little amount of light of the ultraviolet laser ray L2, and the lens 91 is provided for extensively projecting this reflection light upon the position detector 92. The position detector 92 is constructed by, for example, positioning a light receiving element to be dividing into the X and Y directions, thereby to detect the shift amount of the laser ray through calculation of detection signals of those light receiving elements, by means of an electric circuit not shown in the figure. With this, it is possible to make the ultraviolet laser ray emitted from each of the ultraviolet laser ray source 3a and 3b to be incident upon the optical system 70, with stability.

As was explained in the above, with provision of the plural number of the ultraviolet laser ray sources 3, each comprising the solid-state laser device 4 and the wavelength converter device 5 therein, it is possible to selectively change the output of the ultraviolet laser ray, and as a result of this, it is possible to obtain the normal ultraviolet laser ray source, always with certainty, and to perform the inspection of the microscopic patterns by using the ultraviolet laser ray, with continuity and high reliability.

Figure 12:
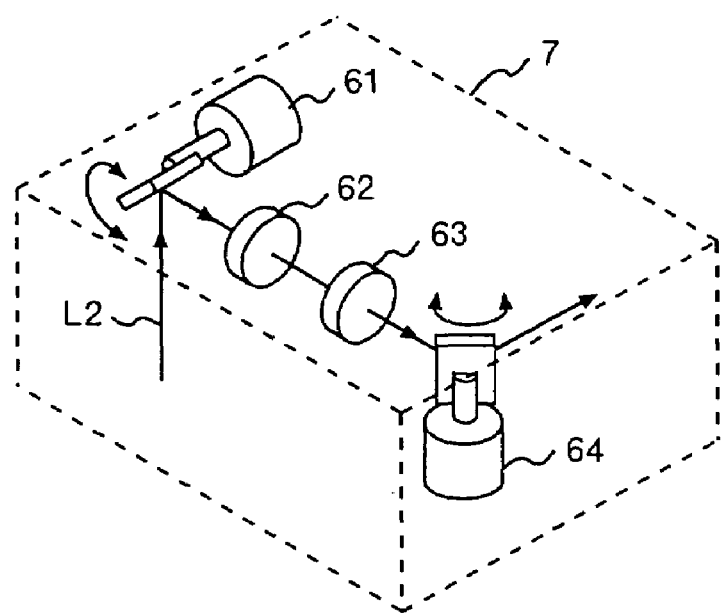
FIG. 12 is a perspective view of showing another embodiment of the optical system for reducing coherence therein.
Figure 13:
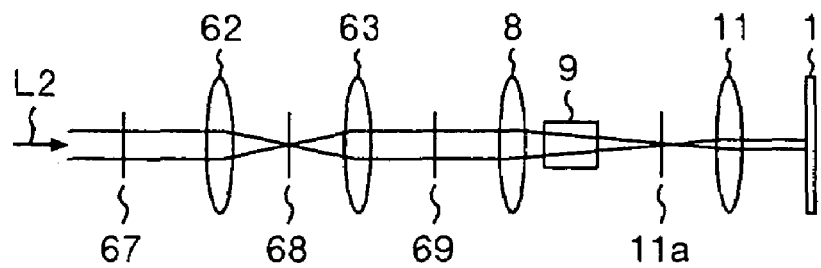
FIG. 13 is a block diagram of showing the optical system which is shown in the FIG. 12.
Figure 14A:
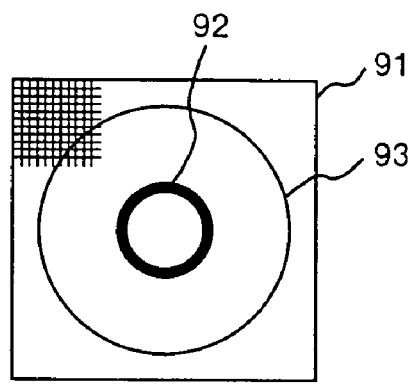
FIGS. 14(a) and (b) are views of showing conditions for zonal illumination (or ring-like illumination), while scanning the ultraviolet laser spot ray on the pupil of an objective lens so as to reduce the spatial coherence therein.

Next, explanation will be given on another embodiment of the coherence reduction optical system 7. In this embodiment, as shown in FIG. 12, the laser ray is scanned in two-dimensional manner by means of a pupil scanning mechanism, which is constructed with two (2) pieces of orthogonal scanning mirrors 61 and 64, thereby being reduced in the coherence thereof, spatially. FIG. 13 is a diagram of the illumination system. The ultraviolet laser ray L2, being emitted from the ultraviolet laser ray source 3 and expanded to a certain size by the beam expander 6, comes to be a parallel luminous flux to be reflected upon the mirror 61 and to be condensed by the lens 62, and thereafter it comes to be a parallel luminous flux, again, through the lens 63 to be condensed upon the pupil 11a of the objective lens 11 by the lens 8. Reference numerals 67 and 69 indicate the reflection positions of the laser light upon the scanning mirrors 61 and 64, and they are in the conjugated relationship with the surface of the test object 1 in the positions thereof. Also, a reference numeral 68 is a surface of a first pupil, being in the conjugated relationship with the pupil 11a of the objective lens 11. Accordingly, through rotational or wobbling control of the scanning mirrors 61 and 64 by means of electric signals, it is possible to scan the ultraviolet laser ray L2 upon the pupil 11a of the objective lens 11, in the two-dimensional manner. The electric signal to be inputted to the scanning mirror 61 or 64 may be a triangle signal or a rectangular signal, etc., for example, and the scanning of the ultraviolet laser ray can be conducted in various shapes, by changing the frequency and/or amplitude of that electric signal. In particular, scanning the ultraviolet laser spot upon the pupil 11a of the objective lens 11 in a zonal (or ring-belt like) manner, as shown in FIGS. 14(a) and (b), by controlling the scanning of the scanning mirrors 61 and 64, respectively, it is possible to perform a zonal illumination through the objective lens 11 upon the test object 1, while reducing the coherence thereof. Further, as will be mentioned later, even in a case that the illumination light is an ultraviolet multi-slit spot beam corresponding to the TDI sensor, it is also possible to remove the optical interference, completely, by positioning the scattering plate after the pupil scanning mechanism which is constructed with the scanning mirrors 61 and 64 mentioned above.

By the way, on the optical path of the illumination light, a mirror 82 is positioned for dividing an amount of illumination light so that it does not impedes the illumination of the test object 1, and it is constructed so that a portion of the illumination laser ray divided by the mirror 82 mentioned above can be observed by means of the TV camera 85. Namely, the light divided by the mirror 82 mentioned above is the ultraviolet laser ray, therefore a screen 83, which emits fluorescence light when that ultraviolet laser ray is incident thereupon, is provided at the position in the conjugated relationship with the pupil 11a of the objective lens 11. As a result of this, expanding the fluorescence light image 92 occurring upon the screen 83 (in the case where the ultraviolet laser ray is scanned in the zonal manner, two-dimensionally) through a lens 84, it is possible to observe such the image 91, as shown in FIG. 14(a), through the TV camera 85. Further, a numeral reference 93 indicates an outer diameter of the pupil 11a of the objective lens 11. And, processing the image 91 outputted from the TV camera 85 in a signal processing circuit 60 shown in the FIG. 18, it is possible to obtain an amount of shifting of the illumination light 92 from the center of the pupil 11a, for example, and this shift amount is fed back to a controller circuit 95, thereby enabling control of the scanning by means of the scanning mirrors 61 and 64 of the coherence reducing optical system 7.

Also, the signal processing circuit 60, encoding the image received by the TV camera 85 into binary values, obtains an area of the illumination by adding up pixels being brighter than a certain value thereof, thereby enabling optimization of an illumination condition (i.e., the illumination σ).

Further, it is needless to say that the scanning of the ultraviolet laser ray by means of the scanning mirrors 61 and 64 is conducted during the storage time of the image sensor 13.

Figure 15:
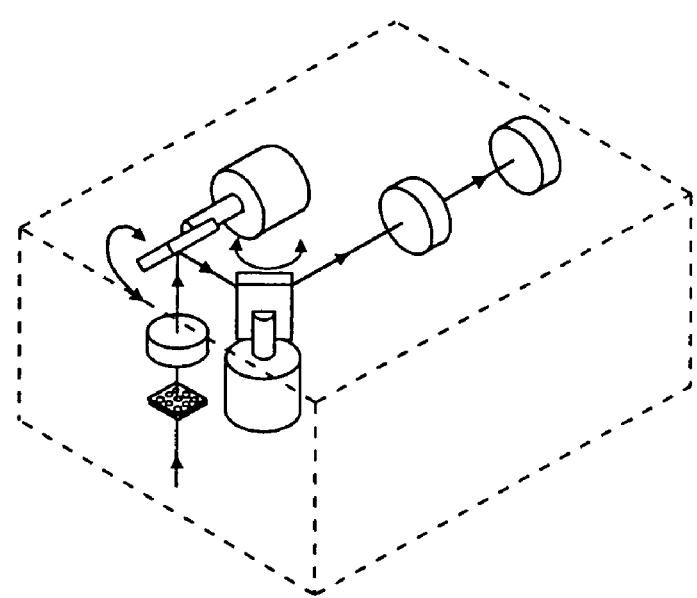
FIG. 15 is a perspective view of showing an embodiment for reducing the spatial coherence therein by using multi-spots.
Figure 16A:
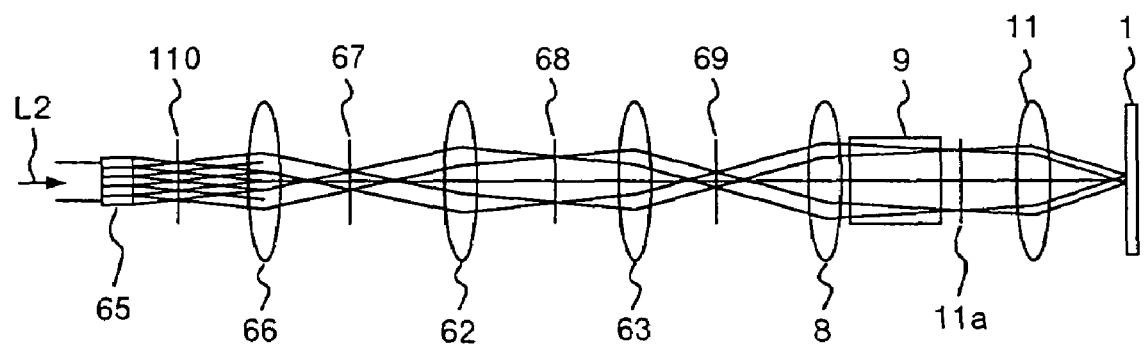
FIGS. 16(a) to (c) are diagrams of showing an optical system for illumination with using the multi-spots.
Figure 16B:
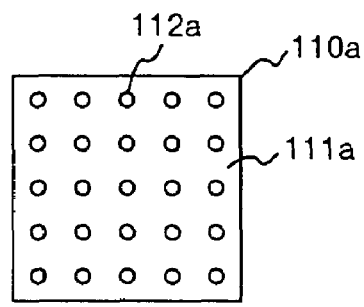
Figure 16C:
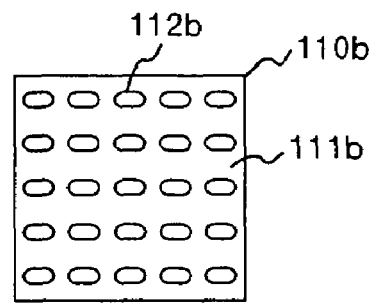
Figure 17A:
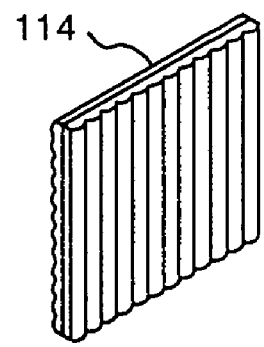
FIGS. 17(a) to (c) are views for showing embodiments of an optical element that forms the multi-spots.
Figure 17B:
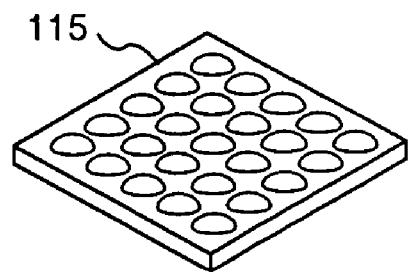
Figure 17C:
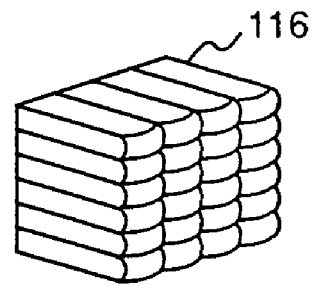

Next, explanation will be given on another embodiment in relation to the condition of illumination. Namely, in this embodiment, the ultraviolet laser ray is irradiated upon the pupil 11a of the objective lens 11, for multi-spot illumination. Since the illumination σ can be gained by conducting the multi-spot illumination in this manner, it is possible to delay the scanning time by means of the scanning mirrors 61 and 64. FIG. 15 is a three-dimensional view of the coherence reducing optical system 7, in which a multi-lens array 65 and a lens 66 are disposed, and FIG. 16 is a diagram of an illumination system using it therein. Namely, the multi-lens array 65 and a lens 66 are added in relation to the incident ultraviolet laser ray L2, thereby making up imaginary multiple sources of the ultraviolet laser rays, and they are condensed upon the pupil 11a of the objective lens 11. Further, a reference numeral 110 shown in FIG. 16(a) indicates a mask for forming the multi-spotlights, in more preferable manner. Also, a reference numeral 110a shown in FIG. 16(b) is a front view of an example of the mask for forming the multi-spotlights, and a reference numeral 110b shown in FIG. 16(c) a front view of another example of the mask for forming the multi-spotlights. Reference numerals 112a and 112b indicate portions for penetrating the light therethrough, while 111a and 111b portions of shutting off the light. As for the means (i.e., the multi-lens array) 65 for making up the imaginary multiple sources of the ultraviolet laser rays, it can be obtained by lens arrays, in which two (2) cylindrical (or renticular) lens arrays 113 are positioned with crossing at right angle, for example, as shown in FIG. 17(a), or by positioning a rod-lens array 115 of disposing small-sized convex lenses two-dimensionally thereon, as shown in FIG. 17(b). However, in a case where the storage type TDI sensor is used as the image sensor, it is necessary to make the multi-spotlights into multi-slit spotlights 140, corresponding to the light receiving surface of the TDI sensor (for example, as was shown in the FIG. 20). For that purpose, as such the means 65 mentioned above, a long and narrow rod-lens array 116, shown in FIG. 17(c), for example, might be used therefor.

Figure 14B:
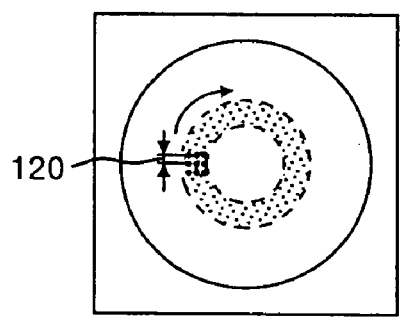

And, FIG. 14(b) shows the scanning condition by the multi-spotlights, which comes to be the zonal illumination upon the pupil 11a of the objective lens 11. In the same manner, the scanning is conducted upon the pupil 11a of the objective lens 11, by the multi-slit spotlights corresponding to the TDI sensor. A pitch 120 between the points of condensing the laser rays upon the pupil 11a of the objective lens 11 can be changed freely, by changing the focal distance of the lens 66, as well as the focal distance(s) of the other lens(es).

According to the present invention, it is possible to achieve an effect of providing the ultraviolet laser-generating device; wherein the wavelength converter device does not receives the ill influence largely, from the heat generated by the non-linear optical elements, and the contaminants can be prevented from adhering upon the optic resonator, as a whole, including the non-linear optical elements therein, with such the simple construction, thereby converting the incident laser ray in the wavelength with high efficiency, and obtaining the long life-time thereof, without reducing the output intensity of the ultraviolet laser ray, as well.

Also, according to the present invention, it is possible to achieve an effect that, when the decrease of output intensity in the ultraviolet laser ray occurs in the wavelength converter device, the investigation of the cause thereof, and the maintenances, including the determination of the necessity thereof, can be performed, easily.

Further, according to the present invention, it is also possible to achieve an effect that the detection and/or the inspection of defects in the microscopic test patterns, which are formed on the test object, such as the semiconductor wafer, etc., can be achieved, with high resolution and high reliability, through the illumination of the ultraviolet laser ray with stable intensity thereof.

What is claimed is:

1. A laser-generating device, comprising:
   a laser ray source for irradiating and emitting a basic wave of laser ray therefrom;
   a wavelength converter device including an optical resonator and a non-linear crystal for receiving the basic wave of laser ray emitted from said laser ray source and for converting it into an ultraviolet laser ray composed of a multiplied high harmonic light of the basic wave of laser ray; and
   a container having an inlet window, upon which the basic wave of laser ray emitted from said laser ray source is incident upon, an outlet window for emitting the ultraviolet laser ray composed of the multiplied high harmonic light of the basic wave of laser ray, a gas inlet port for introducing a gas into the container, a filter disposed at the gas inlet port for filtering the gas introduced from the gas inlet port and supplying filtered gas into the container through the filter, a gas output port for exhausting gas from the container to outside of the container, and installing said wavelength converter device including the optical resonator and the non-linear crystal therein.

2. A laser-generating device according to claim 1, wherein said gas is an inert gas which does not cause chemical reaction with said laser ray.

3. A laser-generating device according to claim 2, wherein said inert gas is nitrogen gas or argon gas.

4. A laser-generating device according to claim 1, wherein said laser-generating device is an ultraviolet laser-generating device.

5. A laser-generating device according to claim 1, further comprising a monitor installed in a wall of the container for monitoring atmospheric pressure inside of the container.

6. A laser-generating device according to claim 1, wherein the gas inlet port is installed in a wall of the container.

7. A laser-generating device according to claim 6, wherein the filter is disposed at a top of the gas inlet port.

8. A laser-generating device according to claim 7, wherein the filter is disposed proximate to a wall of the container.

* * * * *